United States Patent [19]
Doiron et al.

[11] Patent Number: 5,572,996
[45] Date of Patent: Nov. 12, 1996

[54] IN VIVO PHARMACOKINETICS OF PHOTOSENSITIVE DRUGS AND METHOD

[75] Inventors: Daniel R. Doiron, Santa Ynez; John B. Dunn, Buellton, both of Calif.

[73] Assignee: PDT Systems, Inc., Goleta, Calif.

[21] Appl. No.: 587,547

[22] Filed: Jan. 17, 1996

Related U.S. Application Data

[63] Continuation-in-part of Ser. No. 308,288, Sep. 19, 1994, abandoned.

[51] Int. Cl.[6] .................................................. A61B 5/00
[52] U.S. Cl. ............................................ 128/633; 128/665
[58] Field of Search .................................. 128/633, 634, 128/664, 665

[56] References Cited

U.S. PATENT DOCUMENTS

| | | | |
|---|---|---|---|
| 4,718,417 | 1/1988 | Kittrell et al. | 128/634 |
| 5,074,306 | 12/1991 | Green et al. | 128/633 |
| 5,318,023 | 6/1994 | Vari et al. | 128/633 |
| 5,377,676 | 1/1995 | Vari et al. | 128/634 |

Primary Examiner—Angela D. Sykes
Assistant Examiner—Eric F. Winakur
Attorney, Agent, or Firm—Michael G. Petit

[57] ABSTRACT

This invention describes a method for the accurate and sensitive measurement of an exogenous fluorescence chromophore in vivo. The method provides a means for normalizing a typical endogenous fluorescence signal into a relatively narrow band of values for different tissue types. The method employs irradiation of a target tissue at a single excitation wavelength while measuring two narrow bands of emission wavelengths, one of which is principally associated with the endogenous autofluorescence of the tissue while the other is chosen to be characteristic of the exogenous chromophore of interest. An exogenous chromophore is administered to a target tissue in vivo. A fiber optic positioned near the target tissue delivers illuminating excitation light from a light source to the tissue and receives fluorescence light from both exogenous and endogenous chromophores in the tissue and conducts the fluorescence light to a detector. The ratio of the exogenous fluorescence intensity to the endogenous fluorescence intensity is used to calculate the exogenous chromophore concentration in tissue. The temporal change in the ratio provides a measure of the rate of uptake, retention and excretion of the exogenous chromophore by the target tissue.

2 Claims, 3 Drawing Sheets

IN VIVO PHARMACOKINETICS OF PHOTOSENSITIVE DRUGS AND METHOD

This is a continuation-in-part of application Ser. No. 08/308,288 filed 19 Sep. 1994, now abandoned.

BACKGROUND OF THE INVENTION

1. Reference to Copending Patent Application

Reference is made to co-pending application Ser. No. 08/188,946 filed Jan. 27, 1994, entitled "IN VIVO DOSIMETER FOR PHOTODYNAMIC THERAPY" which is a continuation of U.S. patent application Ser. No. 07/786,036 filed Oct. 31, 1991, naming one of the present inventors (Daniel R. Doiron) as the inventor.

2. Prior Art

In photodynamic therapy and many other medical diagnostic and therapeutics applications it is important to measure either the relative or absolute concentration of fluorescent exogenous chromophore in tissues. Such a measurement can be used to diagnose a disease, such as cancer, viral inflection, vascular plaque, etc., or it can be used for determining the therapeutic dosage of a photosensitive drug such as in photodynamic therapy, chemotherapy, or radiation therapy using a radiation sensitizer. Doing such an in vivo fluorescence measurement in a repeatable and/or quantitative manner can be difficult due to a number of variables affecting the magnitude of the fluorescence signal obtained. These variables include:

(i) Tissue optical properties;

(ii) Excitation wavelength extinction coefficient of the exogenous chromophore and intensity of excitation light;

(iii) Fluorescence properties of the exogenous chromophore including:
  (a) Fluorescence quantum yield;
  (b) Binding site;
  (c) molecular environment conditions such as temperature and pH;

(iv) Relative geometry of the excitation and detection systems;

(v) Tissue endogenous chromophore fluorescence interference (also know as autofluorescence or AF); and (vi) Gain characteristics of the detection system.

Many methods have been developed to measure the fluorescence intensity of various chromophores for analytical and diagnostic applications. To overcome the problems noted above, most methods for measuring the fluorescence intensity employ a very rigidly defined geometry requiring control of all parameters effecting the measured signal. For example, typical analytical fluorometers use a standard 90 degree illumination geometry for excitation and detection while using a fixed detection cell path length. The excitation intensity is monitored and ratioed to the measured fluorescence signal. This prior art ratioing method only corrects for variation of the excitation source while not providing any correction for the other parameters. A 90 degree system is not easily adapted for use with partially opaque or turbid materials.

For in vivo measurement of fluorescence a variety of methodologies may be used. One of the most common employs fiber optics and an Optical Multichannel Analyzer (OMA). Such a system generally uses one fiber to deliver the excitation light to the target tissue (tissue under investigation) and one or more fibers to collect and deliver the fluorescence light to the OMA. The OMA uses a diffractive or dispersion grating to spread the light out over a multichannel charge coupled device (CCD). The signal measured in a specific channel of the CCD can then be related to a specific wavelength, (or a narrow band of wavelengths). Such a system provides the general fluorescence emission spectrum of the tissue, but the intensity and shape of this curve will depend on many of the same parameters outlined above. Relating such a spectrum to the level of a specific chromophore requires the normalization of the spectrum along with some detailed spectral analysis to determine the portion of the fluorescence signal which is signal is due to the chromophore of interest. This is particularly difficult if the chromophore of interest is exogenous and there are similar endogenous chromophores present. The flurorescence spectra intensity and curve shape will vary significantly from tissue to tissue samples having either the same or different histology.

Recently a great deal of work has been published and patented on the use on in 9 vivo fluorescence spectroscopy of endogenous chromophores to determine the histological or pathological state of a particular tissue without taking a tissue biopsy. Such methods are based on the difference between the shape and/or intensity of the fluorescence emissions spectrum between normal tissue and diseased tissue. While such methods have been used for diagnosing and/or locating diseased tissue, they have not been applied to in vivo kinetic studies of photosensitive drugs in a particular tissue. It is of particular interest to determine the pharmacokinetics of a particular exogenous chromophore in vivo.

SUMMARY OF THE INVENTION

This invention describes a method for the accurate and sensitive measurement of an exogenous fluorescence chromophore in vivo. The method overcomes many of the problems associated with in vivo fluorescence measurement using prior art methodology. The methodology used compensates for many of the variables effecting the fluorescence signal, as noted earlier, while also permitting the typical endogenous fluorescence signal, i.e. autofluorescence, to be normalized into a relative narrow band of values for a variety of tissue types. This latter feature permits the system to be more sensitive in measuring the endogenous fluorescence signal and therefore provide more accurate and quantitative data.

The method of the present invention employs excitation at a single excitation wavelength while measuring two narrow bands of emission wavelengths, one of which is principally associated with the endogenous autofluorescence of the tissue while the other is chosen to be characteristic of the exogenous chromophore of interest. Since both of these emission signals are excited by the same excitation light, they will both vary in the same way for many of the parameters previously cited as having an effect on the measured fluorescence intensity. For instance such a system can compensate for variation of the excitation intensity and geometry factors. The ratio used is generally the exogenous fluorescence wavelength signal divided by the endogenous fluorescence wavelength signal, due to the fact that the endogenous fluorescence signal is almost always present so that the ratio does not approach infinity as the exogenous signal goes to zero.

The features of the invention believed to be novel are set forth with particularity in the appended claims. Other features and advantages of the present invention will be apparent to those skilled in the art from the following detailed description of the preferred embodiment and the attached drawings, in which:

DESCRIPTION OF THE METHOD

Figure 1:
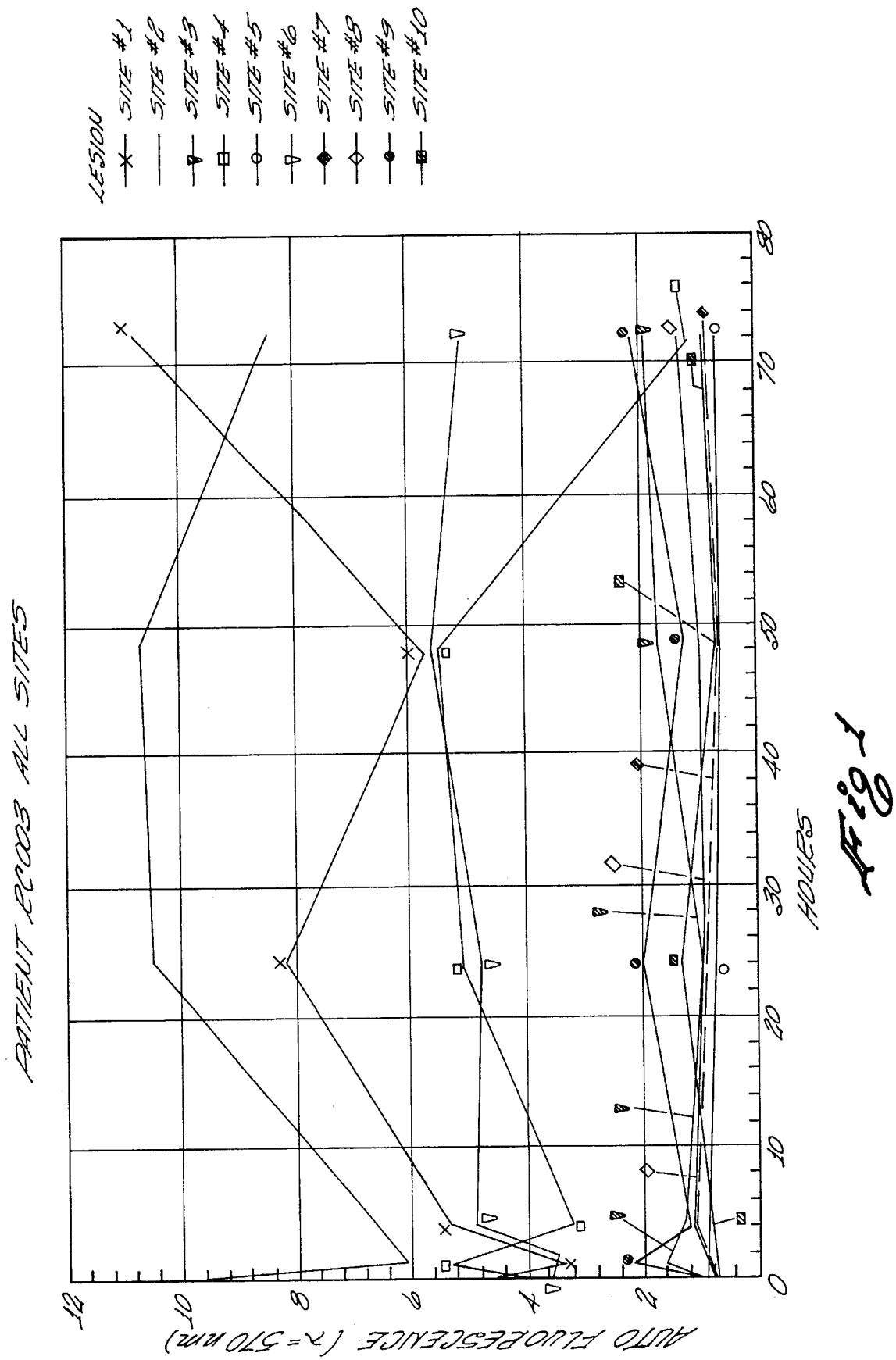
FIG. 1 shows the variation in autofluorescence at 570 nm (excitation wavelength=442 nm) in various sites on a human patient with time.

The use of the ratio of the exogenous chromophore fluorescence intensity to the autogenous fluorescence intensity in the-manner described above generally requires that the signal gain associated with both the autofluorescence and target chromophore fluorescence be tightly controlled, since-small changes in the gain of either channel can significantly alter the ratio of the two signals. In addition, magnitudes of the both fluorescence signals can vary over many decades, five or more, due to the dependence of the measured fluorescence emission on the excitation irradiance and on the distance between the illumination source and the tissue. Each of these parameters vary with the inverse of the distance squared; together they vary the signal according to the inverse of the distance to the fourth power. To overcome the problems associated with these large variation in signal and therefore improve the dynamic range of device, an automatic ranging, or automatic gain control (AGC) system is used. An AGC varies the gain in both channels simultaneously, and equally, so that the actual ratio does not change even though the actual magnitude of the fluorescence signal may change 10,000 times.

One of the present inventors (in a co-pending patent application) has shown that such ratioing concepts permit accurate compensation for signal variation with distance and excitation intensity. The novelty of the present invention is the finding that the use of such ratioing concepts also allows for the relative normalization of the baseline AF for a variety tissues into a relative narrow range of values. This, in turn, permits the accurate and sensitive measurement of the exogenous chromophore fluorescence intensity in-vivo. Surprisingly, such a normalization has not been noted by any other investigators prior to the invention thereof by the present inventors and provides a significant advantage in measuring exogenous chromophore levels in-vivo. In the prior art the signal ratios have only been used to compensate for many of the variables previously mentioned in order to look at intrinsic fluorescence signal differences, and in no way has it been shown to relatively normalize the tissue AF such that a more sensitive and accurate measurement of the exogenous fluorescence can be made.

EXAMPLE

Rats used as an in-vivo model to demonstrate the novelty and utility of the present method. Twenty-four hours prior to measurement the animals were injected either with a control solution, (carrier vehicle), or various concentrations of the exogenous chromophore, tin ethyl etiopurpurin, (SnET2).

SnET2 is a synthetic chlorophyll analogue used in photodynamic light therapy (PDT) that has a relatively weak fluorescence emission, (Quantum yield of 0.01), an emission peak at 670 nm, and a maximum absorption/excitation at 440 nm. At measurement time the animals where anesthetized and then surgically opened to allow measurement of the fluorescence in various tissues. The measurement system used had the following characteristics:

(a) A single fiber was used to deliver excitation light;

(b) Excitation light was derived from a HeCd laser at 442 nm, 1 mm total power delivered to the tissue;

(c) The excitation light was delivered to the target tissue by means of a fiber optic. Fluorescent light emitted by both exogenous and endogenous chromophores in the target tissue was conducted back to the measuring instrument by means of a bundle of smaller optical fibers surrounding the fiber delivering excitation light to the target tissue. Some of these fiber where directed to one PMT (photomultiplier tube) detector filtered for a 570 nm endogenous autofluorescence while the others (12 fibers) were coupled to a PMT filtered at 670 nm for detecting the SnET2 emission;

(d) Autoranging of the gains of the PMTs over five decades;

(e) A display of the 570 (Autofluorescence), 670 (SnET2), signals and the ratio of the two;

(f) An internal reference standard for setting the gain of each PMT prior to each use;

(g) Computer data storage.

The system operates by a foot paddle or a panel button. Activating either one causes the 23 system to take a reading in 1.6 seconds and store it in the display and computer memory. Prior to each use the illuminating probe excitation output is set to 1 mw but this is not necessary due to the ratioing concept.

Table 1 shows the control values for a variety of tissues in Weister Furth rats. In the Tables contained herein, CF represents the intensity of the exogenous chromophore fluorescence emanating from a target tissue whereas AF represents the intensity of the fluorescence emitted by endogenous chromophores the target tissue which has not received exogenous chromophores. The animals were injected with either a vehicle (Table 1) or Tin Etiopurpurin (SnET2) (Table 2) prior to measurement. Excitation was at 442 nm and exogenous fluorescence was measured at 670 nm. The values range from about 0.2 to 0.5 and are highly repeatable (less than 2% average deviation and 10% deviation between tissue of the same type).

TABLE 1

Weister Furth Male Breeder Rats
Vehicle Only

| Tissue | CF | AF | Ratio (CF/AF) |
| --- | --- | --- | --- |
| Kidney | 0.25 | 0.63 | 0.40 |
| Liver | 0.34 | 0.85 | 0.40 |
| Spleen | 0.038 | 0.08 | 0.48 |
| Fat | 0.066 | 0.21 | 0.31 |
| Prostate | 0.31 | 0.84 | 0.37 |
| Muscle | 0.13 | 0.55 | 0.24 |
| Heart | 0.34 | 0.11 | 0.32 |

TABLE 2

Weister Furth Male Breeder Rats
4.0 mg/Kg SnET2, 24 hrs post injection

| Tissue | Control | Data (n = 4) [± SD] |
|---|---|---|
| Kidney | 0.40 | 3.94 ± 0.29 |
| Liver | 0.40 | 35.5 ± 8.17 |
| Spleen | 0.48 | 5.07 ± 1.00 |
| Fat | 0.31 | 48.33 ± 11.9 |
| Prostate | 0.37 | 2.26 ± 0.66 |
| Muscle | 0.24 | 3.42 ± 0.38 |
| Heart | 0.32 | 3.10 ± 1.39 |

The "Control" column in Table 2 presents the ratio of the fluorescence intensity measured at the exogenous chromophore wavelength to the endogenous chromophore fluorescence intensity in target tissue of laboratory animals which were injected with vehicle only. The column headed "Data (n=4)" shows the ratio of the exogenous chromophore fluorescence intensity to the fluorescence intensity (AF) of the endogenous chromophore in the same animal when vehicle plus tinetiopurpurin, an exogenous chromophore used for phototherapy of cancer, is administered.

Note that the ratio of the chromophore fluorescence intensity to the endogenous fluorescence intensity is far greater in the dosed tissue significantly greater than those obtained for the control animals. A small correction can be made for the endogenous autofluorescence by subtracting the control values from the drug containing tissue to give a NET RATIO. This method permits compensation for background tissue difference while permitting accurate and sensitive measurement of the exogenous chromophore presence in the tissue. Chemical extraction of the SnET2 from the tissue allows correlation of the in-vivo drug concentration to the Ratio signal as shown in Table 3 below. Such a correlation would not be accurate or easily done with out using the Ratio concept.

TABLE 3

Spraig Dawley Rats
0.0, 1.0, 2.0, & 4.0 mg/Kg SnET2
Liver and Kidney

| Injected Dose (mg/Kg) | Net Ratio | Extraction (μg/g) |
|---|---|---|
| Liver: | | |
| 1.0 | 17.8 ± 2.15 | 13.2 ± 0.91 |
| 2.0 | 30.0 ± 5.5 | 27.2 ± 2.5 |
| 4.0 | 50.1 ± 12.8 | 59.2 ± 8.9 |
| Kidney: | | |
| 1.0 | 1.73 ± 0.42 | 1.87 ± 0.14 |
| 2.0 | 2.48 ± 0.14 | 3.56 ± 0.11 |
| 4.0 | 4.24 ± 0.90 | 5.49 ± 0.54 |

Figure 2:
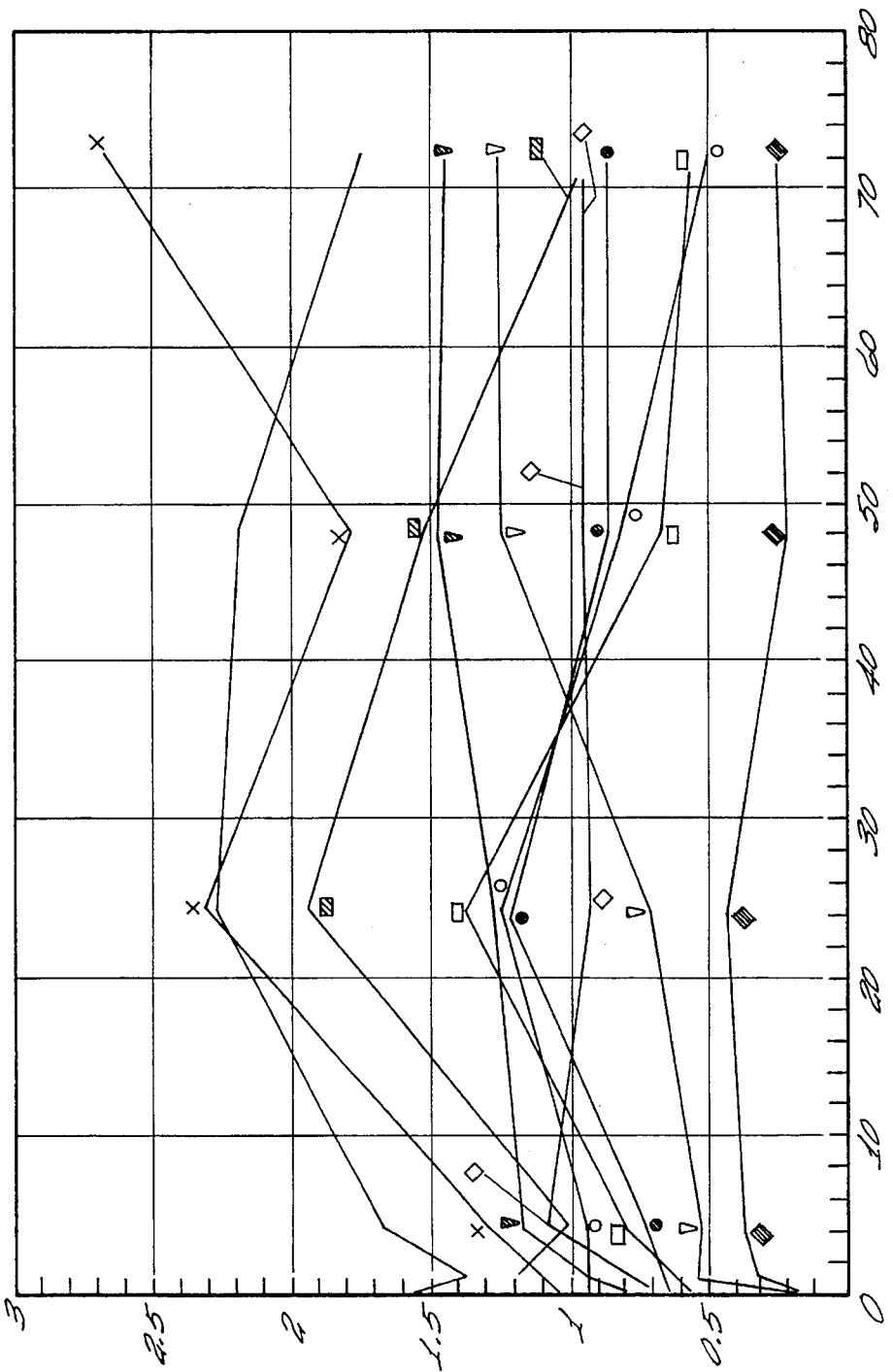
FIG. 2 shows the variation in chromophore fluorescence at 670 nm (excitation wavelength=442 nm) with time in a person injected with SnET2.
Figure 3:
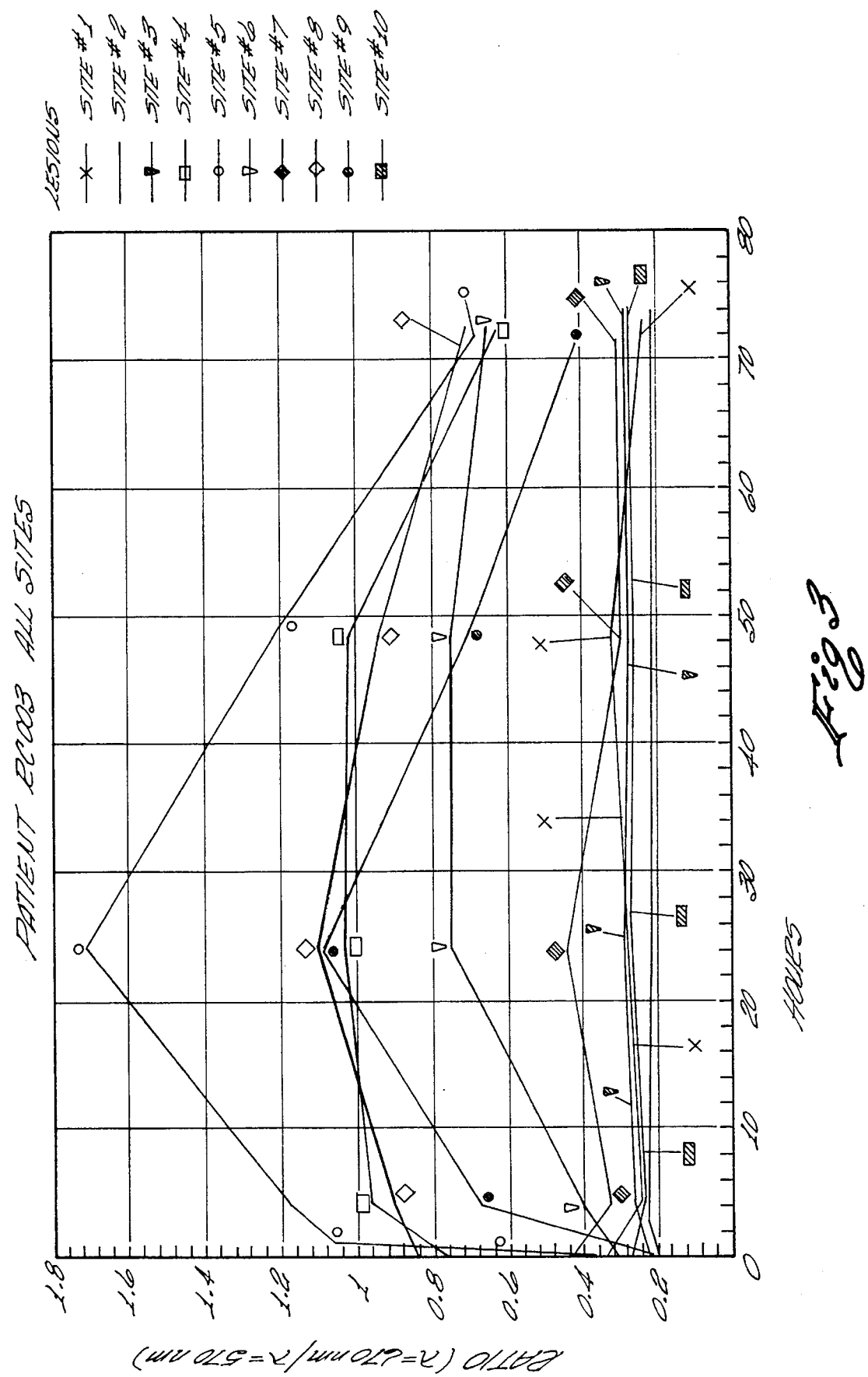
FIG. 3 shows the variation in the ratio of the exogenous fluorescence (at 670 nm) to the intensity of the autofluorescence (at 570 nm) with time at a variety of sites in a human patient.

FIG. 1 presents data from an actual human subject injected with SnET2 for the treatment of a number of skin cancers. A number of normal i.e. control sites, and tumor sites were measured prior to the SnET2 injection, (0.4 mg/kg) and at various times post injection. FIG. 1 shows the autofluorescence signal, which varies greatly with location and time. FIG. 2 shows the SnET2 fluorescence which also greatly varies with site and time, but clearly no trend in the kinetics of drug uptake and concentration change with time can be discerned from the data. FIG. 3 shows the Net Ratio for this data. Clearly from this figure it is clear that the tumors take up the drug significantly more than the control/normal sites and that the optimum time for maximal uptake is 24 hours post injection. Exposure of these areas to red light to introduce a therapeutic response (SnET2 is a photosensitizer) gave a response correlating to the magnitude of the ratio signal. In summary, it is clear from the data provided that the method employing the measurement of the intensity of the exogenous chromophore fluorescence to the autofluorescence of a tissue provide a more accurate means for measuring the pharmacokinetics of an exogenous fluorescing chromophore in vivo. The finding is novel and to the inventor's knowledge has not been taught or acknowledged by others either in a patent or publication. Though the method was discovered and developed during the performance of work associated with photodynamic diagnosis and therapy, the utilization of the present method extends to other types of phototherapy. Any application requiring the in vivo monitoring of rate of change of concentration of a fluorescence chromophore in a tissue could use the present method. For example the in vivo pharmacokinetics of fluorescence labeled monoclonal antibodies for diagnostic or therapeutic application, and certain fluorescent antibiotics such as tetracycline, detection of highly proliferating atherosclerosis, among others. The measurement of the temporal change in the concentration of an exogenous chromophore in a target tissue in the presence of a target tissue-associated endogenous chromophore may be accomplished by performing the following steps:

(a) establishing a concentration of an exogenous chromophore in a target tissue within the body of an animal;

(b) illuminating the target tissue with excitation light having a first wavelength which is absorbed by the exogenous chromophore and the endogenous chromophore thereby causing the exogenous chromophore to emit fluorescence light having a maximum fluorescence intensity at a second wavelength and the endogenous chromophore to emit fluorescence light having a third wavelength which is different than the second wavelength;

(c) detecting and measuring the intensity of the fluorescence light emanating from the target tissue at the second wavelength and the third wavelength;

(d) dividing the intensity of the fluorescence light at the second wavelength by the intensity of the fluorescence light at the third wavelength, the resulting quotient being a measure of the concentration of exogenous chromophore in the target tissue; and (e) repeating steps b–d above over a period of time, the rate of change of the quotient providing a measure of the temporal rate of change of the concentration of exogenous chromophore in the target tissue during the period of time.

To perform step (c) above, the fluorescence light emanating from the target tissue is directed, preferably via fiber optic means, to the input port of a fluorescence light detector apparatus operable for separating fluorescence light having the second wavelength from fluorescence light having the third wavelength and detecting and measuring the intensity of each component of the fluorescence light and computing the ratio of the measured intensity. The ratio is then presented to a suitable output device such as a recorder.

What we claim is:

1. A method for measuring a temporal change in a concentration of an exogenous chromophore in a target tissue in the presence of an endogenous chromophore in the target tissue within the body of an animal comprising the steps of:

(a) establishing a concentration of the exogenous chromophore within the target tissue of the animal;

(b) illuminating the target tissue with excitation light having a first wavelength which is absorbed by the exogenous chromophore and the endogenous chromophore and wherein the absorption of the excitation light by the exogenous chromophore and the endogenous chromophore causes the exogenous chromophore to emit fluorescence light having a maximum intensity at a second wavelength and the endogenous chromophore to emit fluorescence light having a third wavelength and wherein the second and third wavelengths are unequal;

(c) directing the fluorescence light into a fluorescence light detection apparatus operable for separating a portion of the fluorescence light having the second wavelength from a portion having the third wavelength;

(d) detecting and measuring the intensity of the portions of the fluorescence light emanating from the target tissue at the second wavelength and the third wavelength;

(e) dividing the intensity of the fluorescence light at said second wavelength by the intensity of the fluorescence light at said third wavelength, the resulting quotient being a measure of the concentration of exogenous chromophore in the target tissue; and (f) repeating steps b–e above over an interval of time to measure the rate of change of the quotient with time, the rate of change of the quotient with time providing a measure of the temporal change in the concentration of the exogenous chromophore in the target tissue during the interval of time.

2. The method of claim 1 wherein said step of illuminating includes delivering said excitation light having said first wavelength to said target tissue by means of a fiber optic having (a) a proximal end in optical communication with a source of light having said first wavelength; and (b) a distal end in optical communication with said target tissue and further includes maintaining a constant position of the distal end with respect to said target tissue remains constant during said interval of time.

* * * * *